(12) United States Patent
Atkinson et al.

(10) Patent No.: US 6,275,288 B1
(45) Date of Patent: Aug. 14, 2001

(54) GAS CELL FOR DETECTION OF TRACE GASES VIA INTRACAVITY LASER SPECTROSCOPY

(75) Inventors: George H. Atkinson; Markus A. Wolperdinger, both of Tucson, AZ (US); Jeffrey S. Pilgrim, Santa Fe, NM (US)

(73) Assignee: Innovative Lasers Corp., Tucson, AZ (US)

( * ) Notice: Subject to any disclaimer, the term of this patent is extended or adjusted under 35 U.S.C. 154(b) by 0 days.

(21) Appl. No.: 09/291,359

(22) Filed: Apr. 14, 1999

(51) Int. Cl.$^7$ .............................. G01N 1/10; G01N 21/35
(52) U.S. Cl. ..................... 356/246; 356/326; 356/437; 356/440; 250/339.13
(58) Field of Search ..................... 356/244, 246, 356/326, 328, 300, 436, 437, 438, 439, 440; 250/339.12, 339.13, 343

(56) References Cited

U.S. PATENT DOCUMENTS

| | | | |
|---|---|---|---|
| 3,998,557 | * 12/1976 | Javan | 356/407 |
| 5,689,334 | 11/1997 | Atkinson et al. | 356/326 |
| 5,723,864 | 3/1998 | Atkinson et al. | 250/339.13 |
| 5,742,054 | 4/1998 | Atkinson | 250/339.13 |
| 5,747,807 | 5/1998 | Atkinson et al. | 250/339.13 |
| 5,841,533 | 11/1998 | Atkinson | 356/326 |
| 5,917,188 | * 6/1999 | Atkinson et al. | 250/339.13 |
| 6,028,310 | * 2/2000 | Atkinson et al. | 250/339.13 |
| 6,075,252 | * 6/2000 | Atkinson et al. | 250/339.13 |

OTHER PUBLICATIONS

Atkinson et al, "Diode Laser–Pumped Laser System For Intracavity Laser Spectroscopy", U.S. Ser. No. 08/971,862, filed on Apr. 17, 1998.

Atkinson et al, "Linear Cavity Laser System For Intracavity Laser Spectroscopy", U.S. Ser. No. 08/971,861, filed on Nov. 17, 1997.

* cited by examiner

Primary Examiner—Hoa Q. Pham
(74) Attorney, Agent, or Firm—David W. Collins (57) ABSTRACT

A gas cell is provided for detection of trace gases via intracavity laser spectroscopy. The gas cell comprises a gas cell body having a long body axis, an interior hollow portion along the long body axis, and two end portions, each end portion having two opposed surfaces, one surface of each the end portion cut to an angle with respect to the long body axis and including a laser-transparent window on each face defining ends of the interior hollow portion. The angle is dependent on operating wavelength of the spectrometer and refractive index of the window material at the operating wavelength. Each end portion is provided with a gas line connection in the proximity of the opposed surface, one gas line for introducing a sample gas into the interior hollow portion and the other gas line for exhausting the sample gas from the interior portion. Further, a gas cell holder is provided for supporting and positioning the gas cell. The gas cell holder comprises: (a) front, back, top, and bottom surfaces for encompassing the gas cell; and (b) multiple means for providing multiple degrees-of-freedom movement of the gas cell. The combination of the gas cell and the gas cell holder provides a compact laser resonator cavity. The gas cell holder provides the gas cell with multiple degrees of freedom of adjustment and maintains the position of the gas cell after alignment.

23 Claims, 6 Drawing Sheets

GAS CELL FOR DETECTION OF TRACE GASES VIA INTRACAVITY LASER SPECTROSCOPY

TECHNICAL FIELD

The present invention is directed generally to intracavity laser spectroscopy (ILS), and, in particular, is directed to a gas cell for ILS.

BACKGROUND ART

Gas measurement systems often require specifically designed gas cells to provide a well-defined flow of gas through the gas analyzer and to contain the sample gas in a sealed environment, separated from the environment of the analyzer. With regard to these criteria, gas cells must simultaneously meet several different and very demanding objectives, encompassing (1) aspects of gas supply, gas handling and material related issues, and (2) effects caused by the incorporation of the sample gas cell into the measurement system as they influence the operational properties of the analyzer.

To comply with gas supply, gas handling, and material related aspects of the gas measurement system, gas cells must meet the following criteria: (i) they must facilitate the supply of sample gas to the analyzer without exposing the analyzer to sample gas, thereby preventing contamination of sample gas with gas molecules present in the environment of the analyzer; and (ii) the materials comprising the gas cell and in contact with the sample gas, wetted materials hereafter, must be chemically inert with respect to the sample gas, thereby preventing contamination of the sample flowing in the gas cell.

To be compatible with the operational criteria of the gas measurement system, the gas cell incorporated into the analyzer must fulfill one of two general designs: (i) gas cells can be constructed in a way that they introduce minimal, or ideally, no alteration of the operational parameters of the measurement system, a design which is particularly demanding in the case of laser based optical devices; or (ii) gas cells can be constructed in a way that they sustain the operation of the analyzer while deliberately altering the performance parameters of the analyzer. The alteration of the analyzer performance is directly associated with properties of the gas cell itself, e.g., interference patterns caused by cell windows. This approach is often limited to a particular combination of gas cell and optical analyzer.

Regardless of the approach, internal geometry, sample volume and flow characteristics of the gas cell determine the timely response of the analyzer to sample gas concentration changes and can greatly influence the performance of the measurement system. Thus, the gas cell must be optimized in design to minimize response time of the analyzer while maintaining the other desired objectives.

A gas cell optimized for minimum alteration to the operation of the measurement system, complying with the requirements described in the previous sections and suitable for trace gas detection via intracavity laser spectroscopy (ILS) is described herein. Because of its unique and versatile design that minimizes detrimental optical effects within the gas measurement system, the range of potential applications for this gas cell can encompass virtually any optically based application involving gas detection or laser spectroscopy that requires a gas cell.

DISCLOSURE OF INVENTION

In accordance with the present invention, a gas cell is provided for detection of trace gases via intracavity laser spectroscopy, using an intracavity laser spectrometer. The gas cell comprises a gas cell body having a long body axis, an interior hollow portion along the long body axis, and two end portions, each end portion having two opposed surfaces, one surface of each the end portion cut to an angle with respect to the long body axis and including a laser-transparent window on each face defining ends of the interior hollow portion. The angle is dependent on operating wavelength of the spectrometer and refractive index of the window material at the operating wavelength. Each end portion is provided with a gas line connection in close proximity to the opposed surface, one gas line for introducing a sample gas into the interior hollow portion and the other gas line for exhausting the sample gas from the interior portion.

Further, a gas cell holder is provided for supporting and positioning the gas cell. The gas cell holder comprises:

(a) front, back, top, and bottom surfaces for encompassing the gas cell;

(b) multiple means for providing multiple degrees-of-freedom movement of the gas cell; and (c) means for holding the gas cell in a fixed position after positioning.

The combination of the gas cell and the gas cell holder provides a compact laser resonator cavity. The gas cell holder provides the gas cell with multiple degrees-of-freedom of adjustment and maintains the positioning of the gas cell after alignment.

BEST MODES FOR CARRYING OUT THE INVENTION

Reference is now made in detail to a specific embodiment of the present invention, which illustrates the best mode presently contemplated by the inventors for practicing the invention. Alternative embodiments are also briefly described as applicable.

General Description of the Gas Cell

The gas cell described herein is designed to direct a stream of sample gas through the intracavity laser region of an ILS trace gas sensor, to encapsulate the sample gas within a chemically inert environment and to eliminate cross-contamination between sample gas and molecules present in the sensor environment. The choice of wetted materials (typically, ultra-pure stainless steel, quartz, indium, nickel, or polymeric materials) minimizes, or even eliminates, the potential of sample gas contamination caused by materials in direct contact with the gas. The gas cell allows the supply of a wide range of different sample gases, including toxic, hazardous or corrosive gases to various gas sensor implementations suitable for trace gas detection based on ILS methodology; examples of ILS patents which disclose and claim apparatus and/or methods of detection include U.S. Pat. No. 5,689,334, issued Nov. 18, 1997; U.S. Pat. No. 5,723,864, issued Mar. 3, 1998; U.S. Pat. No. 5,742,054, issued Apr. 21, 1998; U.S. Pat. No. 5,747,807, issued May 5, 1998; and U.S. No. 5,841,533, issued Nov. 24, 1998; examples of additional ILS patents include U.S. Pat. No. 6,028,310, issued Feb. 22, 2000, and U.S. Pat. No. 5,917,188, issued Jun. 29, 1999, all assigned to the same assignee as the present application.

The gas cell comprises a metal body, stainless steel gas lines (typically ¼ inch) with standard VCR end fittings to provide connection to the sample gas supply system, and viewing port windows with appropriate mechanical and optical properties attached and sealed to each end of the gas cell body. The specific geometry of the gas cell body, as well as physical properties and shape of the viewing port windows, greatly minimize disturbances of the laser resonator in which the gas cell is located.

Gas flow through the assembled and sealed gas cell is achieved by directing sample gas through a central bore along the long axis of the gas cell body, entering and exiting the gas cell body through flexible gas lines which are attached perpendiculary to both ends of the body. These gas lines can be connected to the sample gas supply system via standard VCR fittings.

A unique gas cell holder, integrating a multiple degree-of-freedom adjustment and lock-down mechanisms, guarantees the best possible alignment of the gas cell within the laser resonator and an extremely stable fixation of the aligned gas cell. The gas cell holder also serves as a mount to attach the gas cell to the laser resonator platform.

Due to the small gas sample volume (typically less than 5 cc) and the simple internal geometry of the gas cell, it exhibits a very fast response to sample gas concentration changes. The physical dimensions of the gas cell are compatible with very small trace gas sensor footprints as required for trace gas detection via ILS applications; see the ILS issued patent and pending patent applications cited above.

The gas cell is virtually maintenance free after the optical alignment has been concluded and no periodic readjustment of cell body or windows is necessary.

Specific Requirements for Gas Cell and Gas Cell Components

The described gas cell must meet a set of stringent criteria that simultaneously constitute a unique set of design requirements for a wide range of applications:

1. The gas cell must be placed within the optical resonator of a laser cavity. The following criteria have to be fulfilled:
   (a) The gas cell must have viewing port windows which transmit the wavelength of the laser with sufficient efficiency to permit the stable operation of the laser above threshold. This can be achieved by specially polished windows with transmission and surface properties chosen to minimize absorption and scattering losses in the wavelength range of laser operation.
   (b) The gas cell viewing port windows must be adjustable to minimize losses in the optical resonator. This can be achieved by cutting the gas cell end portions to a characteristic angle suitable for the specific operational conditions of the analyzer, and by positioning the gas cell windows at that angle by attaching them to the gas cell end surfaces. The gas cell angle is defined with respect to the incident laser beam and is determined by the operational wavelength range of the laser resonator and the refractive index of the window material at a given wavelength in this range. Table I summarizes theoretical values of gas cell angles calculated for different laser wavelength ranges and some typical window materials. Other ranges and materials than listed are possible and can be employed in a similar way. In a typical example, utilizing quartz windows at a laser wavelength of approximately 1.5 $\mu$m, the gas cell angle is approximately 34.7 degrees.

TABLE I

Typical Gas Cell Angles for Different Laser Wavelength Ranges and Window Materials

| Laser wavelength range ($\mu$m) | Window material | Refractive index of window material | Angle of gas cell end faces (degrees) |
|---|---|---|---|
| <0.5 | UV grade Silica | >1.4623 | <34.4 |
| 0.5–1.5 | Infrasil[1] | 1.4624–1.4447 | 34.4–34.7 |
|  | BK7[2] | 1.5210–1.5006 | 33.2–33.7 |
| 1.5–2.5 | Infrasil | 1.4447–1.4300 | 34.7–35.0 |
| 2.5–3.5 | ZnSe | 2.4409–2.4351 | 22.3 |
| >3.5 | ZnSe | <2.4351 | >22.3 |

Notes:
[1]Infrasil is a tradename for a fused quartz having a low -OH content, available from Heraeus;
[2]BK7 is a well-known borosilicate crown optic glass, available from Schott Glass.

The optimum alignment of the gas cell windows has to be established with the windows attached to the gas cell within the laser beam. This can be achieved by a multiple degree-of-freedom optical cell holder.

(c) The gas cell must not introduce effects such as Fabry-Perot interference that would significantly alter the intensity distributions of the laser output. This can be achieved by wedged windows with a wedge angle between 1 and 5 degrees along the long axis of the window.
   (d) The gas cell must be locked and kept in a stable position after adjustments have been finalized to prevent optical misalignment of the laser caused by a mechanical movement of the gas cell. This can be achieved by a unique lock-down mechanism facilitated by the gas cell holder.

2. The gas cell must minimize the volume of sample gas contained within the intracavity laser region while maintaining stable laser operation and ease of alignment.

3. The gas cell must be designed to effectively contain a flowing or static sample gas and mechanically connect to commercially available gas lines.

4. The gas cell must permit rapid (seconds) exchange of gas contaminants for ILS analysis (e.g., dead volumes or non-laminar flow areas must be minimized).

5. The gas cell must be comprised of materials that are compatible with the chemical composition of the sample gas, which can encompass a wide variety of gases with widely different properties.

6. The gas cell design must ensure that no cross contamination between sample gas flowing inside the gas cell and gas on the outside of the gas cell can occur.

7. The gas cell must be sealed and rugged enough to ensure containment of the sample gas in an environment where the pressure can vary in a wide range from above atmospheric to high vacuum (typically, $\leq 10^{-6}$ Torr).

8. The gas cell must accommodate various and variable real-time sample gas pressure levels from above atmospheric pressure to less than 1 Torr.

9. The gas cell must be maintenance free after the alignment of the sample gas cell has been concluded and the gas cell holder has been locked in a stable position within the laser resonator.

Typical Configuration in Which the Gas Cell is Employed

Due to its versatile design and small footprint, the gas cell of the present invention can be utilized in different configurations suitable for intracavity laser spectroscopy and consumes only minimal space in the laser resonator. A typical laser configuration in which the gas cell 10 can be employed (see, e.g., U.S. Pat. Nos. 5,689,334 and 5,742,054) is displayed in FIG. 1, which depicts a three-mirror laser cavity 12. The range of applications for a gas cell 10 as described herein is not restricted to this laser configuration, however. It has been successfully utilized in various other laser configurations designed for trace gas detection (see, e.g., U.S. Pat. Nos. 5,747,807 and 5,723,864). FIG. 2, for example, depicts a two-mirror laser cavity 12'.

Figure 1:
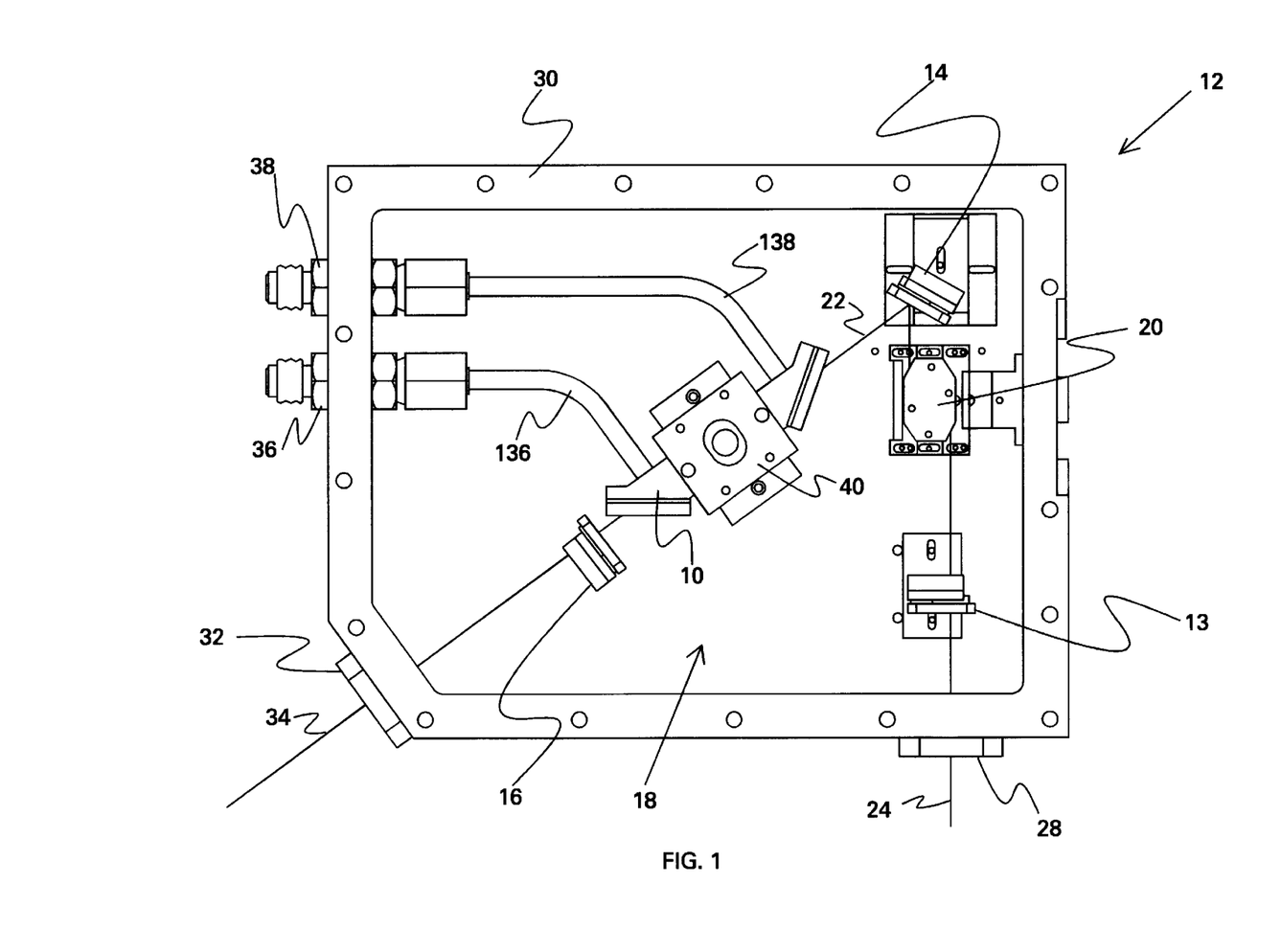
FIG. 1 is a top plan view of a laser resonator apparatus that incorporates the gas cell of the present invention.
Figure 2:
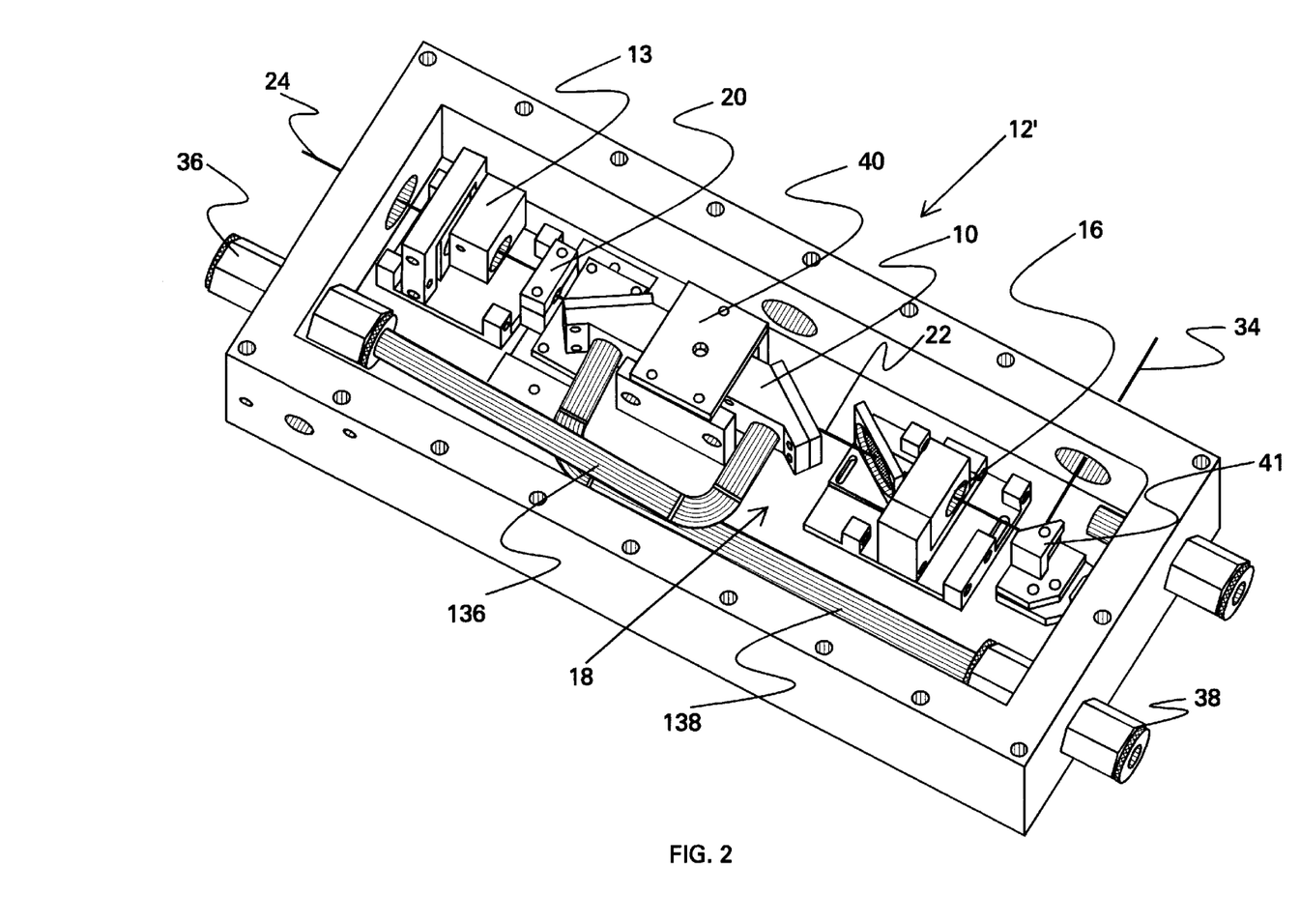
FIG. 2 is a top view, in perspective, of another laser resonator apparatus that incorporates the gas cell of the present invention.

Referring now to FIG. 1, the laser platform specifically described below comprises cavity mirrors 13, 14, 16, which form a three-mirror resonator 18, and a solid state gain medium 20 located inside this resonator. The combination of the cavity mirrors 13, 14, 16 and the gain medium 20 constitute the ILS laser.

Laser light 22 is generated by the gain medium 20 after excitation with pump light 24 of suitable wavelength and intensity entering the resonator 18 through mirror 13, by means of input window 28, and is mostly contained within the resonator region. A small portion of laser light 34 escapes the resonator 18 through mirror 16 by means of output window 32. The gas cell 10 of the present invention is located between cavity mirror 14 and 16 inside the resonator 18 and is aligned in a way that laser light 22 can pass through the gas cell without significant alterations to beam properties or intensity distributions of the laser beam.

The laser resonator 18, gain medium 20, and gas cell 10 can be located in a sealable container 30. Depending on the application, this container 30 is typically made of high purity stainless steel, aluminum, or other suitable material. The container may have various interfaces or ports allowing communication or physical connection between inside and outside: viewing ports 28, 32 for laser light input 24 and output 34, respectively, electrical feed-through connections (not shown), vacuum connections (not shown), and gas line feed-through connections 36, 38 to and from the sample gas cell 10, respectively.

The container 30 may be evacuated to an internal pressure of less than $10^{-6}$ Torr, pressurized to above ambient pressure, or may be kept purged with purified gas at ambient pressure to establish well-defined environmental conditions inside the container. In some cases, the container 30 may be exposed to the ambient environment (typically air) or may be replaced by a simple platform (e.g., a metal plate) on which the ILS laser (cavity mirrors 13, 14, 16 and gain medium 20) and gas cell holder 40 with gas cell 10 can be mounted.

FIG. 2 depicts an alternate laser cavity apparatus 12'. This is a two-mirror apparatus, defined by cavity mirrors 13 and 16. The other elements have the same reference numbers as in FIG. 1. While additional elements are present, such as a mirror or prism 41 for directing the output beam 34 at right angle to the apparatus long axis, these are not germane to the discussion here.

Description of Individual Gas Cell Components

Figure 3:
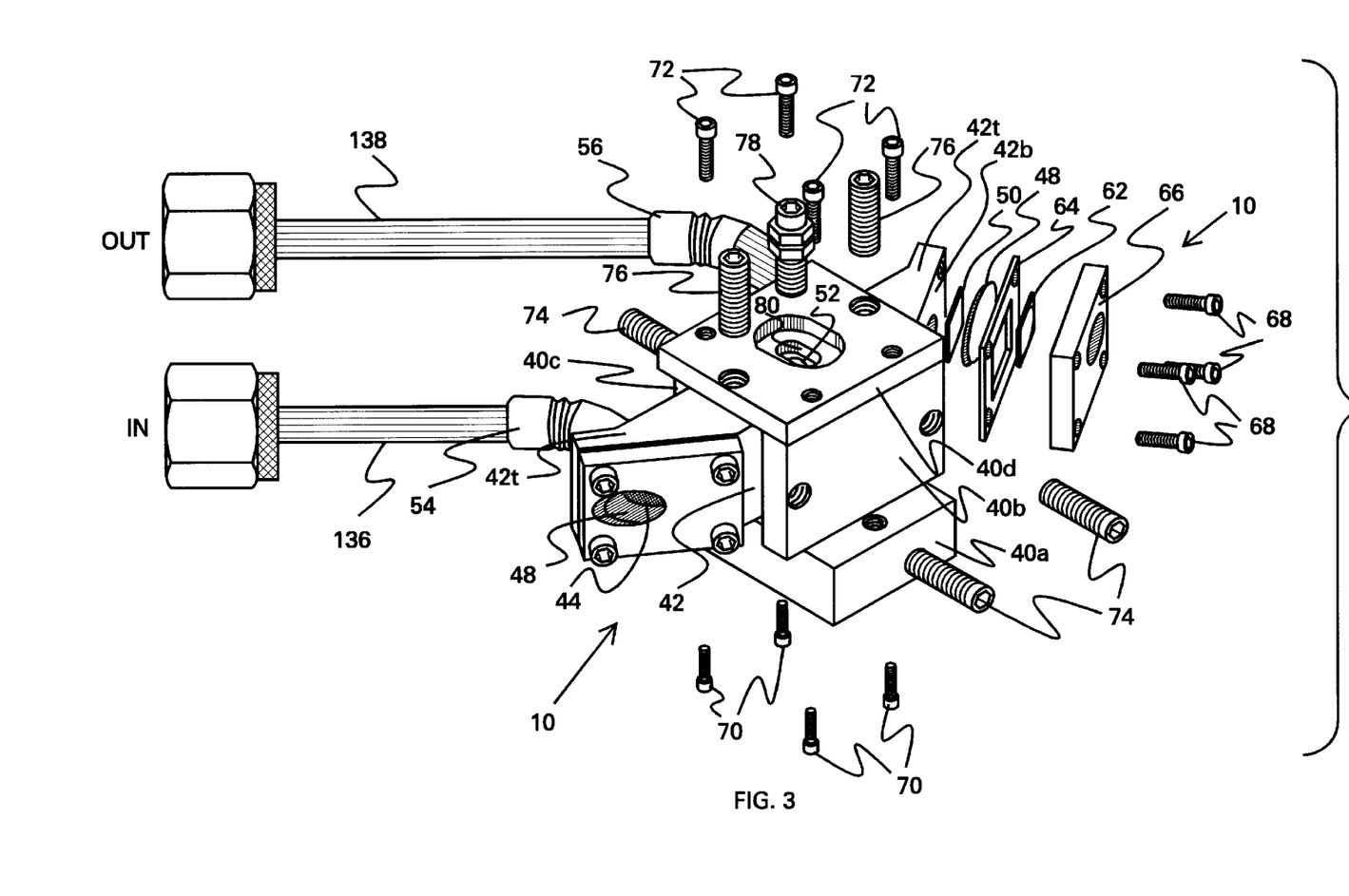
FIG. 3 is a perspective view, partially exploded, showing the gas cell of the invention, together with gas line connections to a gas supply system and a holder for the gas cell.
Figure 4:
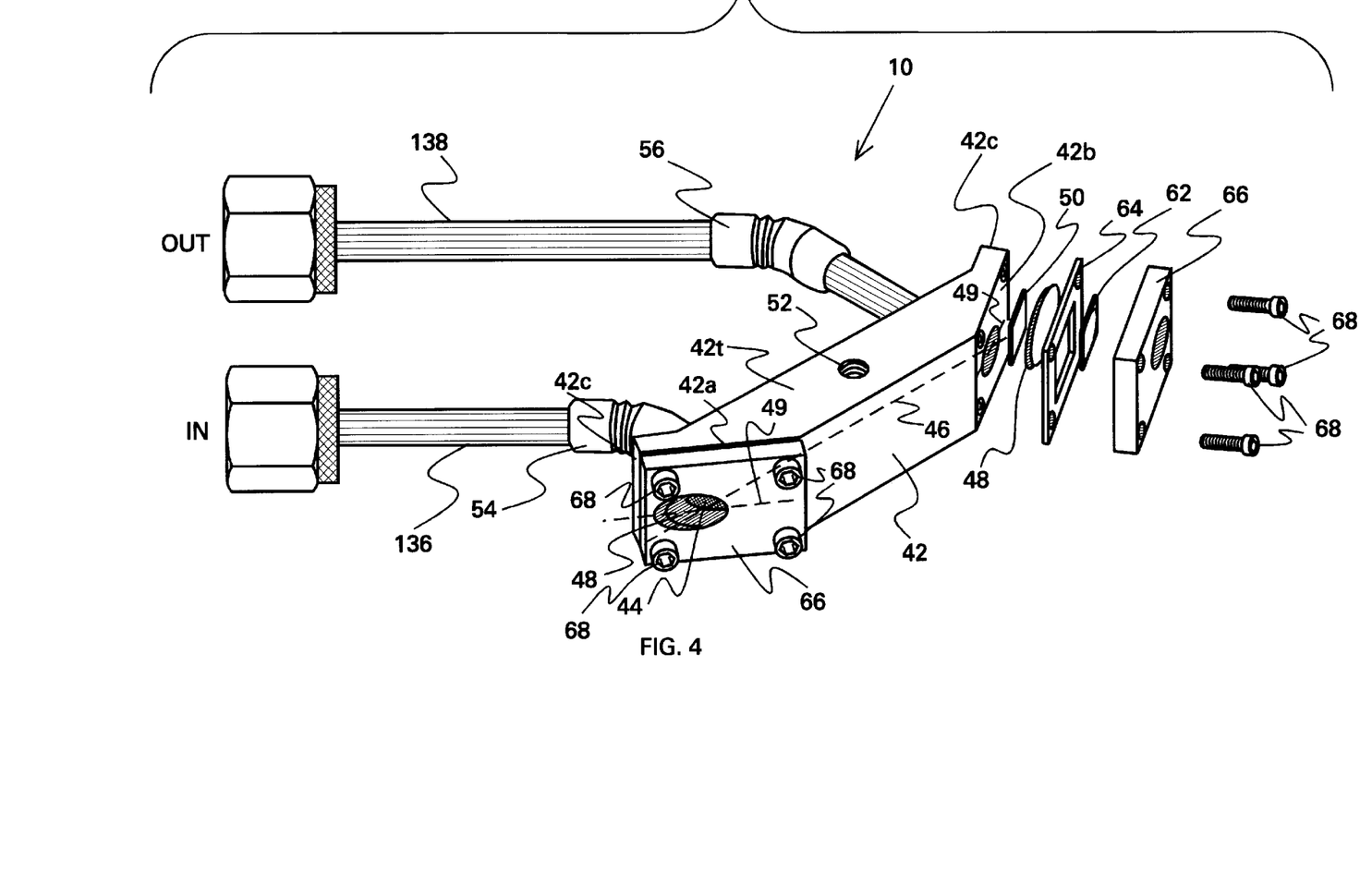
FIG. 4 is a view similar to that of FIG. 3, but without the gas cell holder.
Figure 5:
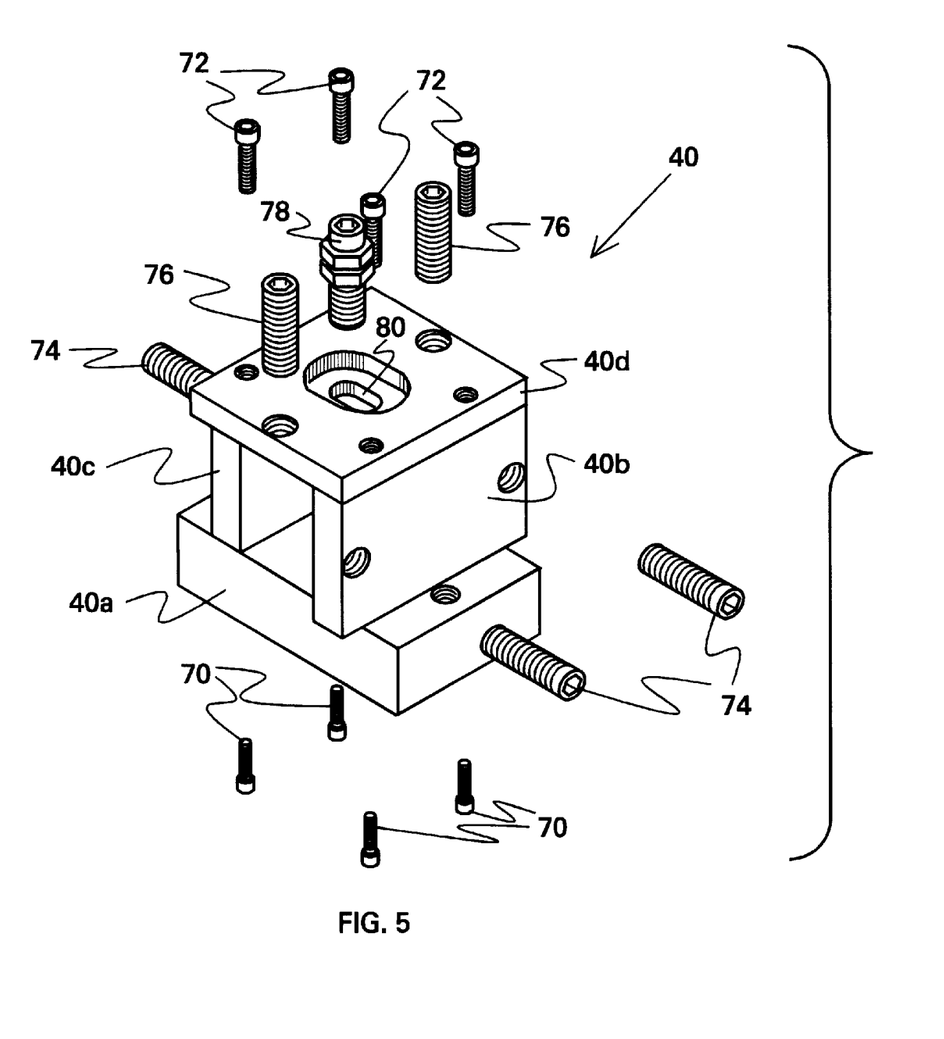
FIG. 5 is a perspective view of the gas cell holder.

Gas cell components are listed and described separately in the following section. The overall assembly of these components, including gas line connections 36, 38 to the gas supply system and a multiple degree-of-freedom gas cell holder 40 with lock-down mechanism is shown in FIG. 3. The assembly of the gas cell body 42 with respective components, without the cell holder 40, is shown in FIG. 4. The assembly of the gas cell holder 40 with the multiple adjustment and lock-down mechanism, without the gas cell body 42 and gas line attachments 136, 138 is shown in FIG. 5.

Mechanical, Dimensional, and Physical Properties of the Gas Cell Body

A gas cell 10 typically utilized in a laser resonator 18, as described in the previous section and shown in FIG. 1 for a three-mirror laser system and in FIG. 2 for a two-mirror laser system, is designed with a square footprint (typically 0.8 inches wide and 3.5 inches long, measured from tip to tip of the cell). The gas cell body 42 is manufactured from ultra-high purity stainless steel 316L/SCQ and has a ¼ inch diameter central bore 44 which is parallel to the long axis 46 of the body to allow for gas flow through the cell 10. A single hole (not shown) with ¼ inch diameter is machined into the gas cell body 42 close to each end 42a, 42b of the cell body perpendicular to the long body axis 46 and connecting to the central bore 44. The gas cell bore 44 and both connecting holes are machined with a surface finish of better than 20 RA. Welded to these connecting holes are ultra-high purity gas lines (typically ¼ inch) 136, 138, which provide connections to the sample gas supply system (not shown) via standard ultra-high purity VCR flanges (typically ¼ inch).

Both ends 42a, 42b of the gas cell body 42 are cut to a specified angle, as described earlier (see Table I). The end surfaces of the gas cell body 42 are machined with a surface finish better than 20 RA and a flatness better than 0.0002 inches to achieve a superior seat for viewing port seals 50. A threaded hole 52 for a ¼ inch 80 pitch fine thread screw is machined in the top surface 42t of the gas cell body 42 to provide adjustability of the gas cell body in a vertical direction in conjunction with the multiple degree-of-freedom gas cell holder 40.

It is essential for any gas cell utilized for high purity applications to minimize sample gas contamination caused by wetted materials (e.g., cell body material, windows, seals, gas lines). Materials in contact with sample gas and especially the gas cell body material, have to be chemically inert to the sample gas and its trace gases. To comply with these requirements, the gas cell body 42 is machined out of a solid block of ultra-high purity stainless steel (typically 316L/SCQ, with low sulfur content for increased corrosion resistance). All internal and external cell body surfaces are mechanically processed to a surface finish of better than 20 RA and typically electrochemically passivated to further improve surface finish and resistance against potential corrosion effects.

Gas Line Attachment to the Gas Cell Body

As mentioned above, a single bore (not shown) is machined perpendicular to the central bore 44 close to each end 42a, 42b of the gas cell body 42. These holes connect to the central bore 44 and provide attachment points for gas lines 136, 138, which are typically ¼ inch ultra-high purity stainless steel 316L gas lines. The gas lines 136, 138 are welded to the perpendicular gas cell body openings in an inert gas environment utilizing a welding method certified for ultra-high purity applications to minimize potential contaminations in the welding zone. Each gas line 136, 138 terminates in standard VCR fittings (typically ¼ inch, not shown), which provide leak-tight connections to the sample gas supply system.

To provide the flexibility required for the optical alignment of the gas cell 10 within the laser resonator 18, a convoluted, or flexible, section, specifically, a bellows section 54, 56, is incorporated in each gas line 136, 138, respectively, approximately one inch away from the gas cell body 42. This region provides the necessary flexibility due to its specific design of convolutions. For optimum flexibility, a number of between 3 and 10 convolutions is required.

Viewing Port Properties and Specific Geometry of Gas Cell End Faces

Both end surfaces 42a, 42b of the gas cell body 42 have to be sealed with viewing port windows 48 with suitable optical properties in a well-defined spatial arrangement to achieve maximum transmittance of the laser wavelength necessary for a stable operation of the laser above threshold. Several different design criteria ensure that these performance requirements can be met:

1. The end faces 42a, 42b of the gas cell body 42 are machined to a specified angle as described earlier (see Table I). Due to the fact that the end faces 42a, 42b of the gas cell body 42 are machined at an angle with respect to the gas cell, the viewing port windows 48 have to be shaped elliptically to achieve a maximum clear aperture for the laser beam traveling through the gas cell. Attaching viewing port windows 48 in the described geometrical configuration allows reflective losses to be minimized on the surfaces of the windows if the polarization properties of the laser beam 22 are carefully matched with the orientation of the windows.

2. Very low reflective and absorptive losses can be achieved with specially polished windows ("superpolished" windows) with transmission and surface properties chosen to minimize absorption and scattering losses in the wavelength range of laser operation. "Superpolished" windows are manufactured according to a proprietary process by Research Electro-Optics (Boulder, Colo.) and exhibit extremely low scattering and reflective losses due to the high surface quality of the windows.

As a further requirement, the gas cell 10 must not introduce effects such as Fabry-Perot interference that would significantly alter the intensity distributions of the laser output. This can be achieved by introducing a slight wedge to the gas cell windows 48, with a wedge angle between 1 and 5 degrees along the long axis 49 of the window. The viewing port windows 48 are attached to both end faces 42a, 42b of the gas cell body 42 in a way that the thicker side of one window is oriented towards the end 42c of the gas cell body 42 and the thicker side of the second window is oriented 180 degrees with respect to the first window.

Figure 6A:
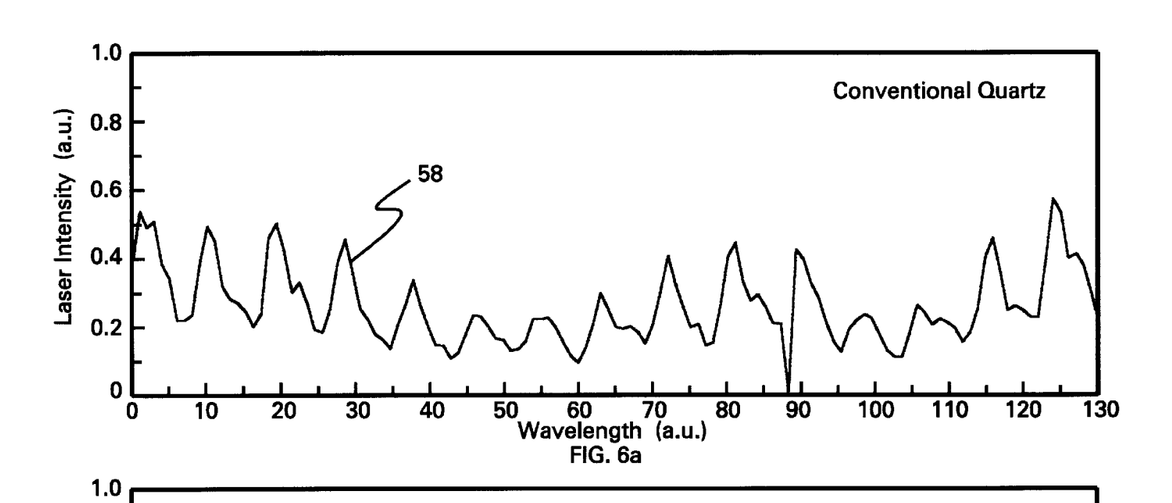
FIG. 6a is a plot, on coordinates of laser intensity (arbitrary units) and wavelength (arbitrary units), depicting the performance of the gas cell of the present invention equipped with ordinary plane parallel quartz windows.
Figure 6B:
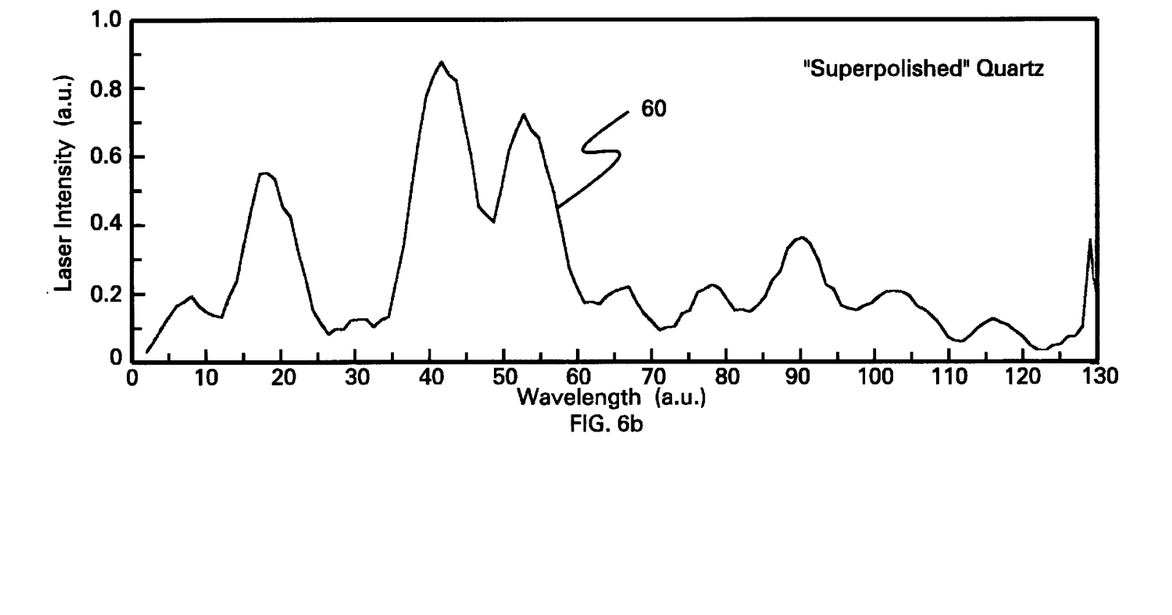
FIG. 6b is a plot similar to that of FIG. 6a, but depicting the performance of the gas cell equipped with wedged and specially processed quartz windows for comparison.

FIGS. 6a and 6b provide a comparison of the performance of a gas cell equipped with different types of windows. FIG. 6a shows the intensity distribution of a laser beam 22 having a wavelength of about 1.4 $\mu$m after passing through a gas cell 10 with ordinary plane parallel quartz windows without special surface treatment. A regular structure superimposed to the spectral output (Curve 58) clearly indicates optical interference effects caused by the gas cell windows. This superstructure is detrimental to the laser performance and to the overall performance of the trace gas measurement system. In the plot shown in FIG. 6b, the same laser beam 22 was sent through a gas cell 10 with wedged and "superpolished" windows. The resulting laser output (Curve 60) does not show any sign of interference structure superimposed on the clearly resolved spectrum.

Viewing Port Attachment to the Gas Cell Body

The attachment and sealing of the viewing port windows 48 to the gas cell body 42 is critical to ensure a contamination-free operation of the gas cell 10. Depending on the type of seal selected for this purpose, permeation rates through the seal below $10^{-9}$ cm$^3$/minute for helium test gas can be achieved. A permeation rate of less than $10^{-9}$ cm$^3$/minute is widely accepted in the semiconductor industry as a tolerable leak rate. Materials utilized for the purpose of sealing viewing port windows 48 against the end surfaces of the gas cell body 42 include metal, typically, indium, nickel, or gold, and polymers, typically, Viton® and Kalrez®. Viton and Kalrez are both fluorocarbon elastomers, and both are available from Dupont de Nemours, Co. (Wilmington, Del.), with Kalrez being the perfluorocarbon version of the elastomer seals utilized.

To achieve a reproducible low leak rate and to guarantee the superior performance of the gas cell 10 in high purity applications, a specific set of components and a procedure for the attachment of these components to the gas cell body must be used. FIG. 4 shows these components and their spatial arrangement with respect to the viewing port windows 48 and the gas cell body 42.

The selected window seal 50 (in the form of an O-ring) is directly attached to the gas cell body 42, followed by the viewing port window 48. To provide constant and stable pressure on the seal, an additional Viton® O-ring 62 is positioned on top of the viewing port window 48 and held in place by a retainer ring 64 with appropriate thickness to achieve the desired compression of the seal. These components are attached to the gas cell body end surfaces 42a, 42b with an ultra-high purity stainless steel metal flange 66 and held in position with four 4–40 bolts 68 located on each corner of the flange. During the sealing procedure, uniform pressure has to be applied to the bolts 68 in a regular pattern until the desired seal quality is achieved and the described arrangement is held in position tightly.

Besides the ability to adjust the flange pressure to the elasticity of the selected seal material, the described viewing port window configuration has the advantage that attached windows 48 and seals 50, 62 can be replaced easily.

Multiple Degree-of-Freedom Gas Cell Mount for Adjustment and Fixation of the Gas Cell Body It is critical for the operation of any laser that optical elements within the laser resonator 18 do not cause significant cavity losses and once aligned do not change their position, e.g., due to mechanical misalignment. Operating a gas cell 10 inside a laser resonator 18 suitable for intracavity laser spectroscopy, as described herein, is especially demanding, since the result of the ILS measurement critically depends on stable laser operation. An optical mount, or gas cell holder, 40 facilitating multiple degrees-of-freedom for adjustment and permanent, highly stable fixation of the gas cell 10 within the laser resonator 18 is presented. The entire mount 40 is manufactured from ultra-high purity stainless steel 316L to provide superior rigidity and positioning stability for the gas cell 10.

To achieve the required accuracy for the adjustment of the gas cell 10 within the laser beam path 22, the gas cell body 42 is mounted in an adjustable multiple degree-of-freedom holder 40; the mount itself is depicted in FIG. 5. This holder 40, and consequently the gas cell 10 mounted on it, can be attached to the container 30 or platform holding the laser resonator 18, and provides the required stable positioning of the gas cell with respect to the laser resonator.

The holder 40 comprises a bottom plate 40a, on which are supported front plate 40b and rear plate 40c. A top plate 40d is supported by the front and rear plates 40b, 40c. Screws 70 secure the front and rear plates 40c, 40c to the bottom plate 40a, while screws 72 secure the top plate 40d to the front and rear plates 40b, 40c.

Four adjustable degrees-of-freedom are available with a unique adjustment and lock-down mechanism combined in one single mount 40. Adjustment screws 74 (three such, two through the front plate 40b and one through the rear plate 40c) provide adjustability of the gas cell 10 in the horizontal direction and a rotational movement around the central adjustment screw 78 in the center of the gas cell body 42 in the horizontal plane. Horizontal movement around the central adjustment screw 78 is facilitated through an elongated hole 80 in top plate 40d. Adjustment screws 76 (two such, both through the top plate 40d) allow for the vertical movement of the gas cell 10 in conjunction with central adjustment screw 78. The same screw combination 76, 78 provides a tilt movement with respect to the long axis 46 of the gas cell body 42 in the vertical plane. These four adjustable degrees-of-freedom provide a wide range of flexibility in aligning the gas cell body 42 within the laser resonator 18 to achieve maximum light transmittance and, consequently, the best possible performance of the laser system.

The locking capability of this mount 40 is implemented in a way that after successful alignment of the gas cell 10 within the laser resonator 18, all adjustment screws 74, 76, 78 can be tightened to lock the gas cell into position. Since there are no springs involved in the design of the cell holder 40 and every direction of adjustment is locked, a slow misalignment after concluded positioning of the gas cell 10 is virtually impossible.

INDUSTRIAL APPLICABILITY

The gas cell assembly, comprising the gas cell and the gas cell holder, of the present invention, is expected to find use in intracavity laser spectroscopy apparatus.

Thus, there has been disclosed a gas cell assembly, comprising a gas cell and gas cell holder, for use in intracavity laser spectroscopic apparatus. It will be appreciated by those skilled in this art that various changes and modifications of an obvious nature may be made, and all such changes and modifications are considered to fall within the scope of the present invention, as defined by the appended claims.

What is claimed is:

1. A gas cell for detection of trace gases in an intracavity laser spectrometer comprising:

a gas cell body having a long body axis, an interior hollow portion along said long body axis, a top surface, and two end portions, each end portion having two opposed surfaces, one surface of each said end portion cut to an angle with respect to said long body axis and including a laser-transparent window on each face defining ends of said interior hollow portion, said angle dependent on operating wavelength of said intracavity laser spectrometer and refractive index of said window material at said operating wavelength, each said end portion provided with a gas line connection in the proximity of said opposed surface, one gas line for introducing a sample gas into said interior hollow portion and the other gas line for exhausting said sample gas from said interior portion, wherein said gas connections each have a flexible section near said gas cell body.

2. The gas cell of claim 1 wherein said gas cell is utilized for high purity applications to minimize sample gas contamination caused by wetted materials, wherein materials in contact with said sample gas are chemically inert to said sample gas and its trace gases.

3. The gas cell of claim 2 wherein said gas cell body is machined out of a solid block of ultra-high purity stainless steel and all internal and external cell body surfaces are mechanically processed to a surface finish of better than 20 RA and electrochemically passivated to further improve surface finish and resistance against potential corrosion effects.

4. The gas cell of claim 1 wherein said viewing port windows are shaped elliptically to achieve a maximum clear aperture for the laser beam traveling through the gas cell.

5. The gas cell of claim 4 wherein each said viewing port windows is sealed and secured to said gas cell body by seals maintained against said window by a flange.

6. The gas cell of claim 1 wherein said viewing port windows are wedged with respect to their long axis to minimize interference effects inside the optical resonator.

7. The gas cell of claim 1 wherein said viewing port windows are selected for low surface scattering losses to minimize the optical losses inside the optical resonator.

8. The gas cell of claim 1 wherein said viewing port windows are selected for suitable absorptive properties to minimize the optical losses inside the optical resonator.

9. The gas cell of claim 1 wherein said gas line connection is welded to said gas cell body by high purity welding techniques.

10. The gas cell of claim 1 wherein said flexible section comprises a bellows, having from three to ten convolutions for optimum flexibility of said gas connections.

11. A gas cell assembly for detection of gases in an intracavity laser spectrometer, said gas cell assembly comprising:

(a) a gas cell comprising a gas cell body having a long body axis, an interior hollow portion along said long body axis, a top surface, and two end portions, each end portion having two opposed surfaces, one surface of each said end portion cut to an angle with respect to said long body axis and including a laser-transparent window on each face defining ends of said interior hollow portion, said angle dependent on operating wavelength of said spectrometer and refractive index of said window material as said operating wavelength, each said end portion provided with a gas line connection in the proximity of said opposed surface, one gas line for introducing a sample gas into said interior hollow portion and the other gas line for exhausting said sample gas from said interior portion; and (b) a gas cell holder for supporting, positioning, and holding said gas cell, said gas cell holder comprising:

(1) front, back, top, and bottom plates for encompassing said gas cell therebetween, (2) multiple adjustable means for providing multiple degrees-of-freedom movement of said gas cell; and (3) means for locking said gas cell in a fixed position after adjustment.

12. The gas cell assembly of claim 11 further comprising a threaded hole for a screw machined in said top surface of said gas cell body to provide adjustability of the said cell body in a vertical direction in conjunction with a multiple axis gas cell holder.

13. The gas cell assembly of claim 11 wherein said gas cell is utilized for high purity applications to minimize sample gas contamination caused by wetted materials, wherein materials in contact with said sample gas are chemically inert to said sample gas and its trace gases.

14. The gas cell assembly of claim 13 wherein said gas cell body is machined out of a solid block of ultra-high purity stainless steel and all internal and external cell body surfaces are mechanically processed to a surface finish of better than 20 RA and electrochemically passivated to further improve surface finish and resistance against potential corrosion effects.

15. The gas cell assembly of claim 11 wherein said viewing port windows are shaped elliptically to achieve a maximum clear aperture for the laser beam traveling through the gas cell.

16. The gas cell assembly of claim 15 wherein each said viewing port windows is sealed and secured to said gas cell body by seals maintained against said window by a flange.

17. The gas cell assembly of claim 11 wherein said viewing port windows are wedged with respect to their long axis to minimize interference effects inside the optical resonator.

18. The gas cell assembly of claim 11 wherein said viewing port windows are selected for low surface scattering losses to minimize the optical losses inside the optical resonator.

19. The gas cell assembly of claim 11 wherein said viewing port windows are selected for suitable absorptive properties to minimize the optical losses inside the optical resonator.

20. The gas cell assembly of claim 11 wherein said gas line connection is welded to said gas cell body by high purity welding techniques.

21. The gas cell assembly of claim 11 wherein said gas connections each have a flexible section near said gas cell body.

22. The gas cell assembly of claim 21 wherein said flexible section comprises a bellows, having from three to ten convolutions for optimum flexibility of said gas connections.

23. The gas cell assembly of claim 11 wherein said multiple means for providing multiple degrees-of-freedom movement of said gas cell comprise:

(a) two adjustment screws through said front surface and one adjustment screw through said back surface, each screw contacting a surface of said gas cell, for providing adjustability of said gas cell in a horizontal direction and a rotational movement around a center of said gas cell in a horizontal plane; and (b) two adjustment screws through said top surface and flanking a third adjustment screw through said top surface, each screw contacting a surface of said gas cell, for providing vertical adjustment of said gas cell and for providing a tilt movement with respect to said long axis of said gas cell in a vertical plane.

* * * * *